(12) United States Patent
Bliven et al.

(10) Patent No.: US 8,633,434 B2
(45) Date of Patent: Jan. 21, 2014

(54) APPARATUS AND METHOD FOR PULSED NEUTRON GENERATION INCLUDING A HIGH VOLTAGE POWER SUPPLY

(75) Inventors: Steven Bliven, Magnolia, TX (US); Yi Liu, Houston, TX (US); Constantyn Chalitsios, Houston, TX (US)

(73) Assignee: Baker Hughes Incorporated, Houston, TX (US)

( * ) Notice: Subject to any disclaimer, the term of this patent is extended or adjusted under 35 U.S.C. 154(b) by 143 days.

(21) Appl. No.: 13/014,208

(22) Filed: Jan. 26, 2011

(65) Prior Publication Data

US 2011/0186722 A1 Aug. 4, 2011

Related U.S. Application Data

(60) Provisional application No. 61/299,748, filed on Jan. 29, 2010.

(51) Int. Cl.
*G01V 5/10* (2006.01)

(52) U.S. Cl.
USPC .................................................... 250/269.4

(58) Field of Classification Search
USPC .................................................... 250/269.4
See application file for complete search history.

(56) References Cited

U.S. PATENT DOCUMENTS

| 1,956,639 | A | | 5/1934 | Dana et al. | |
|---|---|---|---|---|---|
| 3,133,195 | A | * | 5/1964 | Jones et al. | ................ 250/262 |
| 4,387,302 | A | | 6/1983 | Givens | |
| 4,808,368 | A | | 2/1989 | Humphreys | |
| 4,972,082 | A | | 11/1990 | Loomis et al. | |
| 6,141,395 | A | | 10/2000 | Nishimura et al. | |
| 7,446,308 | B2 | | 11/2008 | Gilchrist et al. | |
| 2005/0028586 | A1 | * | 2/2005 | Smits et al. | ................ 73/152.14 |
| 2006/0065429 | A1 | * | 3/2006 | Kim et al. | ................ 174/120 R |
| 2009/0135982 | A1 | * | 5/2009 | Groves | ........................ 376/113 |
| 2010/0252726 | A1 | | 10/2010 | Inanc et al. | |

OTHER PUBLICATIONS

"The Use of Non Linear Permittivity Filters for the Purposes of Stress Grading within Cables," Proceedings of the 7th International Conference on Properties and Applications of Dielectric Materials, Jun. 2003, p. 1210-1213, to Robertson et al.*
Chichester, et al. "Compact Accelerator Neutron Generators". Technology Dec. 2003/Jan. 2004. The industrial Physicist. pp. 22-25.
Smith, et al. "Small Accelerators as Neutron Generators for the Borehole Environment". IEEE Transactions on Nuclear Science, vol. 35, No. 1, Feb. 1988. pp. 859-862.
Notification of Transmittal of the International Search Report and the Written Opinion of the International Searching Authority, or the Declaration; PCT/US2011/023001 Sep. 27, 2011.

* cited by examiner

*Primary Examiner* — David Porta
*Assistant Examiner* — Kenneth J Malkowski
(74) *Attorney, Agent, or Firm* — Cantor Colburn LLP

(57) ABSTRACT

An apparatus for irradiating an earth formation is disclosed. The apparatus includes: a carrier configured to be disposed in the formation; a neutron tube disposed at the carrier and located on an axis; and a high voltage power source disposed at the carrier and electrically connected to the neutron tube, the high voltage power source being offset from the axis.

20 Claims, 7 Drawing Sheets

APPARATUS AND METHOD FOR PULSED NEUTRON GENERATION INCLUDING A HIGH VOLTAGE POWER SUPPLY

CROSS REFERENCE TO RELATED APPLICATIONS

This application claims the benefit of an earlier filing date from U.S. Provisional Application Ser. No. 61/299,748 filed Jan. 29, 2010, the entire disclosure of which is incorporated herein by reference.

BACKGROUND

Pulsed neutron measurement tools are utilized in downhole environments for a variety of purposes, such as neutron based density and porosity measurements, and neutron induced gamma-ray spectral measurements.

Pulsed neutron generators for well logging applications normally consist of a sealed neutron tube, means of generating ions in a portion of the tube and means of extracting and accelerating the ions generated onto a target material. The acceleration of the ions is generally accomplished by way of a power supply capable of providing sufficient voltage to efficiently accomplish the desired reaction. The geometrical constraints associated with a neutron source housing such as a sonde or drill collar, together with the high voltage considerations imposed, are typically addressed by a linear coupling configuration between the high voltage power supply (HVPS) and the neutron generator tube. Such constraints often prevent emitters and detectors from being positioned in measurement devices at optimal locations.

SUMMARY

An apparatus for irradiating an earth formation includes: a carrier configured to be disposed in the formation; a neutron tube disposed at the carrier and located on an axis; and a high voltage power source disposed at the carrier and electrically connected to the neutron tube, the high voltage power source being offset from the axis.

An apparatus for estimating at least one property of an earth formation includes: a carrier configured to be disposed in the formation; at least one detector disposed at the carrier; a neutron tube disposed at the carrier and located on an axis; and a high voltage power source disposed at the carrier and electrically connected to the neutron tube, the high voltage power source being offset from the axis.

A method of estimating at least one property of an earth formation includes: disposing a carrier in a borehole in the earth formation, the carrier including a neutron tube located on an axis and at least one detector; supplying power to the neutron tube by activating a high voltage power source electrically connected to the neutron tube, the high voltage power source being offset from the axis; emitting neutron pulses from the neutron tube into the formation; detecting at least one of neutrons and gamma rays emitted from the formation by the at least one detector; and estimating the at least one property based on at least one of the detected neutrons and the detected gamma rays.

BRIEF DESCRIPTION OF THE DRAWINGS

The subject matter which is regarded as the invention is particularly pointed out and distinctly claimed in the claims at the conclusion of the specification. The foregoing and other features and advantages of the invention are apparent from the following detailed description taken in conjunction with the accompanying drawings in which:

DETAILED DESCRIPTION

Apparatuses and methods for pulsed neutron measurements are described herein. The apparatuses and methods include a pulsed neutron generator including a high voltage power source for supplying accelerating voltage and current, which is configured to allow for effective placement of detectors used in pulsed neutron and other radiation measurements. In one embodiment, the pulsed neutron generator is configured to be disposed in a downhole environment, for example, in a wireline or logging-while-drilling (LWD) well logging application to facilitate measurements such as neutron based density, porosity measurements, and neutron induced gamma-ray spectral measurements. In one embodiment, the pulsed neutron generator includes a high voltage power source in an offset configuration to allow for enhanced measurement capabilities associated with allowing detectors to be more appropriately positioned with respect to a neutron emitting portion of the pulsed neutron generator.

In one embodiment, the tool includes a pulsed neutron source including a neutron tube and a remote high voltage power source, and one or more detectors such as radiation detectors. In one embodiment, the one or more detectors are located proximate to the neutron tube. For example, the neutron tube and the one or more detectors are placed in line with the neutron tube and/or placed adjacent to the neutron tube for optimal response to formation variables.

Figure 1:
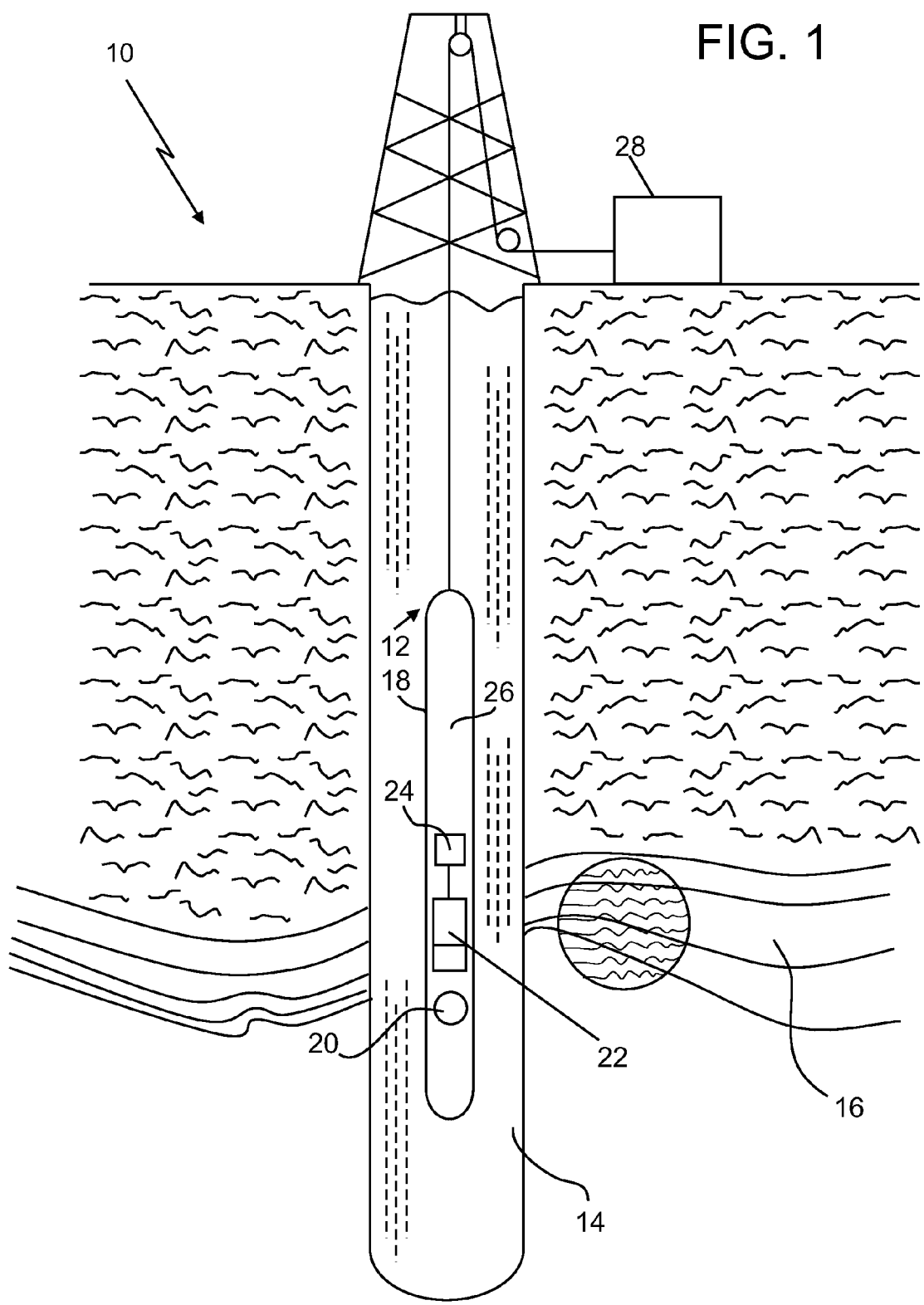
FIG. 1 is a side cross-sectional view of an embodiment of a subterranean well drilling, evaluation, exploration and/or production system.

Referring to FIG. 1, an exemplary embodiment of a subterranean well drilling, evaluation, exploration and/or production system 10 includes a borehole string 12 that is shown disposed in a borehole 14 that penetrates at least one earth formation 16 during a subterranean operation. As described herein, "formations" refer to the various features and materials that may be encountered in a subsurface environment and surround the borehole. In one embodiment, the borehole 14 is a cased borehole or an open borehole. In one embodiment, the borehole string includes a downhole tool 18 such as a well logging tool. In this example, the downhole tool 18 is a wireline tool, but is not limited thereto. For example, the downhole tool 18 can be incorporated with a drill string for logging-while-drilling (LWD) applications, such as when the borehole 14 is not completed with a casing. The downhole tool 18 is not limited to the embodiments described herein, and may be disposed with any suitable carrier. A "carrier" as described herein means any device, device component, combination of devices, media and/or member that may be used to convey, house, support or otherwise facilitate the use of another device, device component, combination of devices, media and/or member. Exemplary non-limiting carriers include drill strings of the coiled tube type, of the jointed pipe type and any combination or portion thereof. Other carrier examples include casing pipes, wirelines, wireline sondes, slickline sondes, drop shots, downhole subs, bottom-hole assemblies, and drill strings.

The downhole tool 18, in one embodiment, is configured as a pulsed neutron spectroscopy tool. The tool 18 includes, for example, at least one pulsed neutron source 20 and at least one detector 22. Examples of the at least one detector include radiation detectors such as gamma ray detectors and neutron detectors. In one embodiment, electronics 24 are also included for controlling the pulsed neutron source 20 and/or the at least one detector 22, and/or for storing, transmitting and/or processing signals and/or data generated by the at least one detector 22. The number of pulsed neutron sources 20 and detectors 22 is not limited. In one embodiment, the at least one gamma ray detector 22 is a scintillation detector that is configured to detect the presence of gamma rays and gamma ray energy levels. Scintillation detectors are generally capable of generating signals and/or data representative of both inelastic and capture gamma ray energy spectra.

The downhole tool 18 includes a housing 26 such as a sonde configured to house at least the neutron source 20 and the at least one detector 22. In one embodiment, the housing also includes the electronics 24. In one embodiment, the tool 18 is equipped with transmission equipment to communicate ultimately to a surface processing unit 28. Such transmission equipment may take any desired form, and different transmission media and methods may be used. Examples of connections include wired, fiber optic, and wireless connections.

Figure 2:
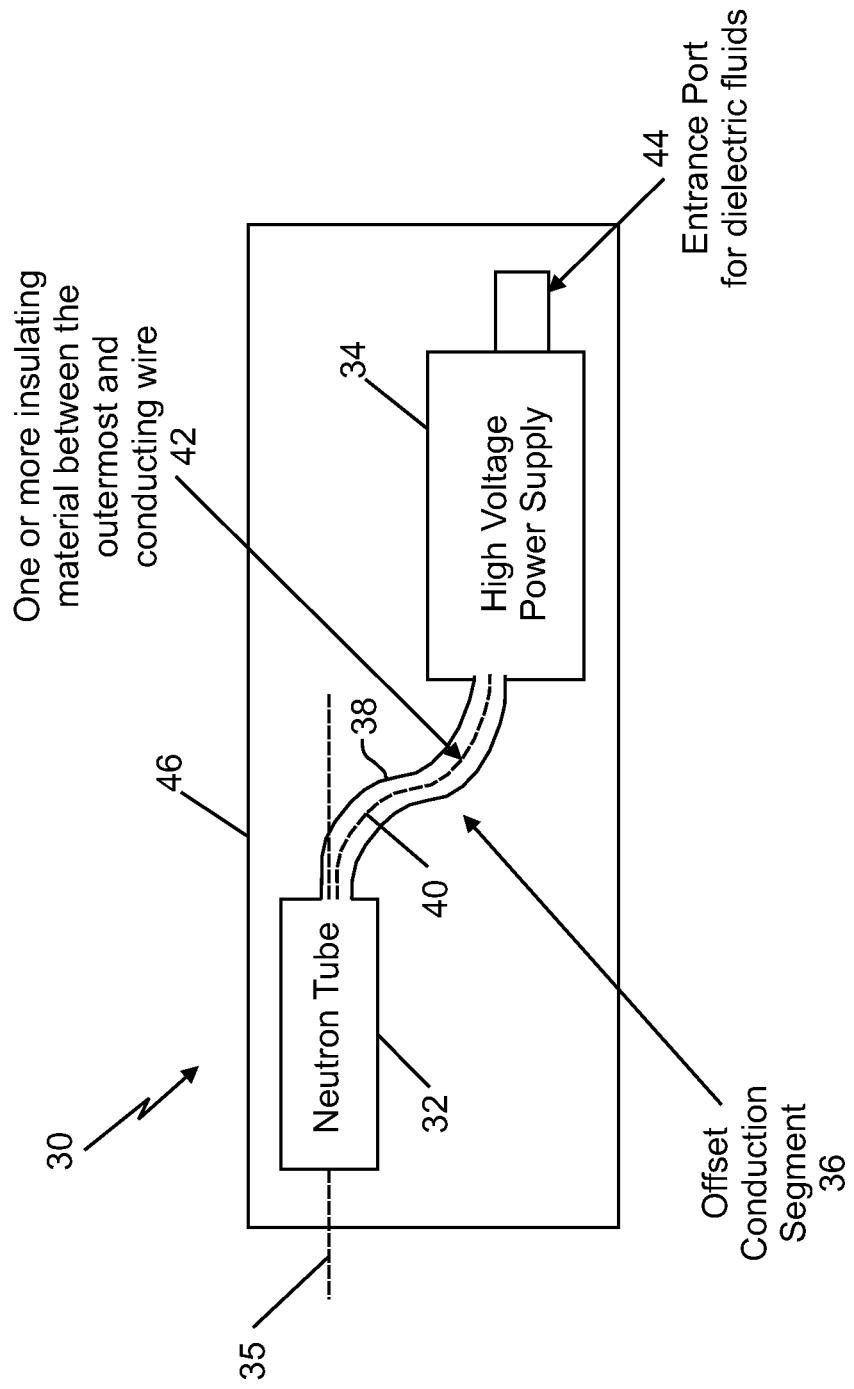
FIG. 2 is a side cross-sectional view of an embodiment of a tool including a neutron tube and a high voltage power source.

Referring to FIG. 2, an exemplary embodiment of the tool 18 includes a neutron source or neutron generator 30 that includes a neutron tube 32 electrically connected to a high voltage power supply (HVPS) 34. In one embodiment, "high voltage" refers to a voltage of about 75 kilovolts (kV) or greater. In one embodiment, the HVPS 34 is configured to supply a voltage of at least about 90 kV. As described herein, a "neutron tube" refers to any device configured to accelerate ions and emit neutrons in response to the application of appropriate energy, such as by the HVPS 34. The neutron tube 32 accordingly acts as a neutron emitter or source and may include various components for emitting neutrons, including ion sources, ion optic elements, and beam targets. The components are disposed in a housing, such as a vacuum tight enclosure. In one embodiment, the neutron tube 32 is a cylindrical tube, although any suitable shape or configuration may be used.

In one embodiment, the HVPS 34 is positioned remotely from the neutron tube 32 at a selected distance and location relative to the neutron tube 32 in a housing suitable for disposition in a downhole environment, such as a sonde or cartridge. The HVPS 34 may be the largest geometrical component of the neutron source 30. The remote positioning of the HVPS 34, or as alternately considered, the remote positioning of the neutron tube 32, allows detectors to be positioned at locations that would not otherwise be allowed. In one embodiment, the HVPS 34 is at an offset position relative to the neutron tube 32. For example, the neutron tube 32 is located on an axis 35, and the HVPS 34 is offset from the axis 35. The axis 35, in one embodiment, is the major axis of the neutron tube 32, although the axis 35 may intersect the neutron tube 32 at any desired location and have any desired orientation. In one example, "offset" refers to a position at which the major axis or other location in the HVPS 34 does not intersect the axis 35.

The HVPS 34, in one embodiment, is electrically connected to the neutron tube 32 via at least one conductor 36 capable of transmitting high voltage electricity. In one embodiment, the conductor 36 is an offset conduction segment 36 that can be curved or bent, or otherwise configured to effect an electrical connection between the neutron tube 32 and the HVPS 34. The offset conduction segment 36 can be bent to various shapes or directions. In one embodiment, the offset conduction segment 36 includes a support structure including, for example, one or more solid dielectric supports having selected voltage withstanding capability, and a ground plane to complete an electrical circuit between the neutron tube 32 and the HVPS 34. The offset conduction segment 36 is, in one embodiment, a tubular and/or cylindrical structure, although any suitable shape may be employed. In one embodiment, the ground plane includes an exterior conductive housing 38 having a conductive wire 40 and one or more insulating materials 42 disposed therein. The insulating materials 42 include one or more solid dielectric materials. In one embodiment, the insulating materials 42 include one or more gaseous and/or liquid dielectric materials that may be disposed within the exterior housing 38 and/or introduced into the exterior housing 38 via, for example, an entrance port 44 located in the HVPS 34 or at another desired location.

In one embodiment, the neutron tube 32, the HVPS 34 and the offset conduction segment 36 are installed in a housing 46. The housing 46 may be made from any desired metallic or other material capable of withstanding downhole environments. Examples of such materials include materials chosen to reduce or minimize radiation production, such as titanium, stainless steel, and alloys including superalloys (e.g., Inconel™, Special Metals Corporation). The shape of the housing 46 may be cylindrical, but is not limited thereto. The shapes and sizes of the housing 46, the neutron tube 32, the HVPS 34 and the offset conduction segment 36 can have different shape and sizes.

Figure 3:
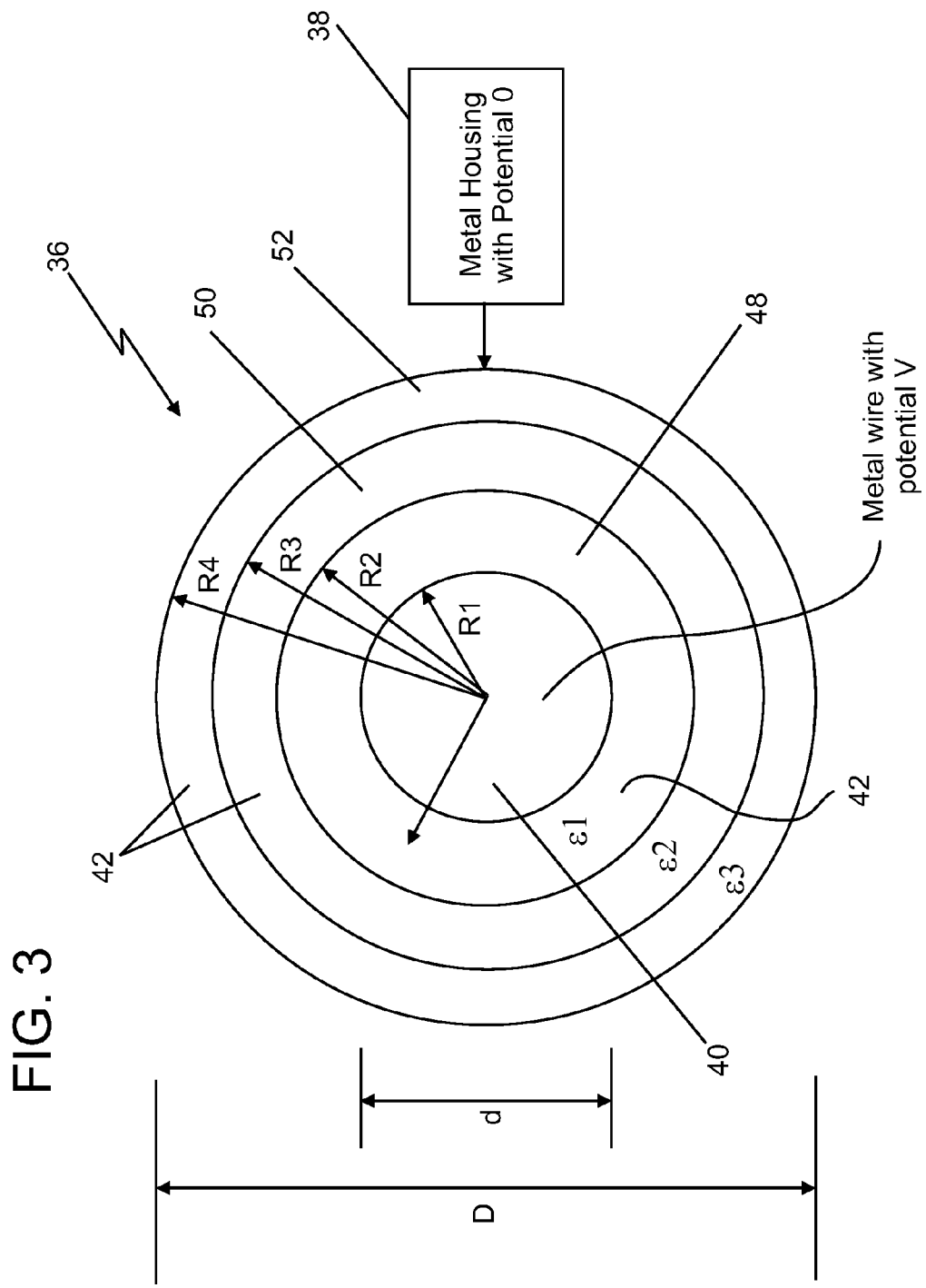
FIG. 3 is an axial cross-sectional view of an offset conduction segment of the tool of FIG. 2.

Referring to FIG. 3, in one embodiment, the offset conduction segment 36 includes a metal conductor such as the wire 40 and various insulating materials 42 for support of the wire 40 and/or control of electric stresses around the wire 40. The wire 40, for example, is a metal wire with a diameter optimized to reduce electric stress on the supporting insulation materials 42.

The wire 40 has a first diameter "d" and the conductive housing 38 has a greater second diameter "D". The ratio of d to D may be selected or optimized based on the dielectric properties of the insulating materials 42, which in some embodiments are configured as structural support members of the offset conduction segment 36. In one embodiment, the insulating materials 42 include multiple dielectric materials 48, 50 and 52 each having differing permittivities "∈". The dielectric materials 48, 50 and 52 may be chosen to provide mechanical support and/or for the control of electric gradients or stresses such that catastrophic high voltage breakdown can be eliminated or reduced.

In the example shown in FIG. 3, the conduction segment 36 includes three layers of dielectric materials. Although this embodiment includes three cylindrical layers, the number and shape of such layers are not limited thereto. For example, the dielectric layers may be any combination of solid, liquid and/or gaseous layers. Having one or more solid layers may provide sufficient mechanical support to allow one or more gaseous and/or liquid dielectric layers to be included.

In one embodiment, the dielectric layers 48, 50 and 52 are arranged to control electric stresses, for example, by making the electric field from the high potential wire 40 to the grounded exterior housing 38 more uniform than an electric field resulting from a single dielectric material.

In the example shown in FIG. 3, an inner dielectric layer 48 surrounds the wire 40 (having a radius "R1" and an applied potential "V") and has a permittivity "∈1" and an outer diameter "R2", an intermediate dielectric 50 surrounds the inner layer 48 and has a permittivity "∈2" and an outer diameter "R3", and an outer dielectric layer 52 surrounds the intermediate layer 50 and has a permittivity "∈3" and an outer diameter "R4". The exterior housing 38 is grounded, surrounds the outer layer 52 and has an inner diameter incrementally greater than "R4". The diameter of each layer may be chosen based on the permittivity of the layer material. For example, for a material with a given dielectric constant or permittivity, the thickness or diameter is selected to keep the maximum magnitude of fields in the layer below the dielectric strength of the material for given temperatures, such as for elevated temperatures. Such elevated temperatures include, for example, the temperatures typically present in downhole environments. In another example, the diameter and/or permittivity of each layer is selected so that the electric field is approximately proportional to 1/x at the interface of two different layers, where "x" is a radial distance from the central axis of the wire 40.

Figure 4:
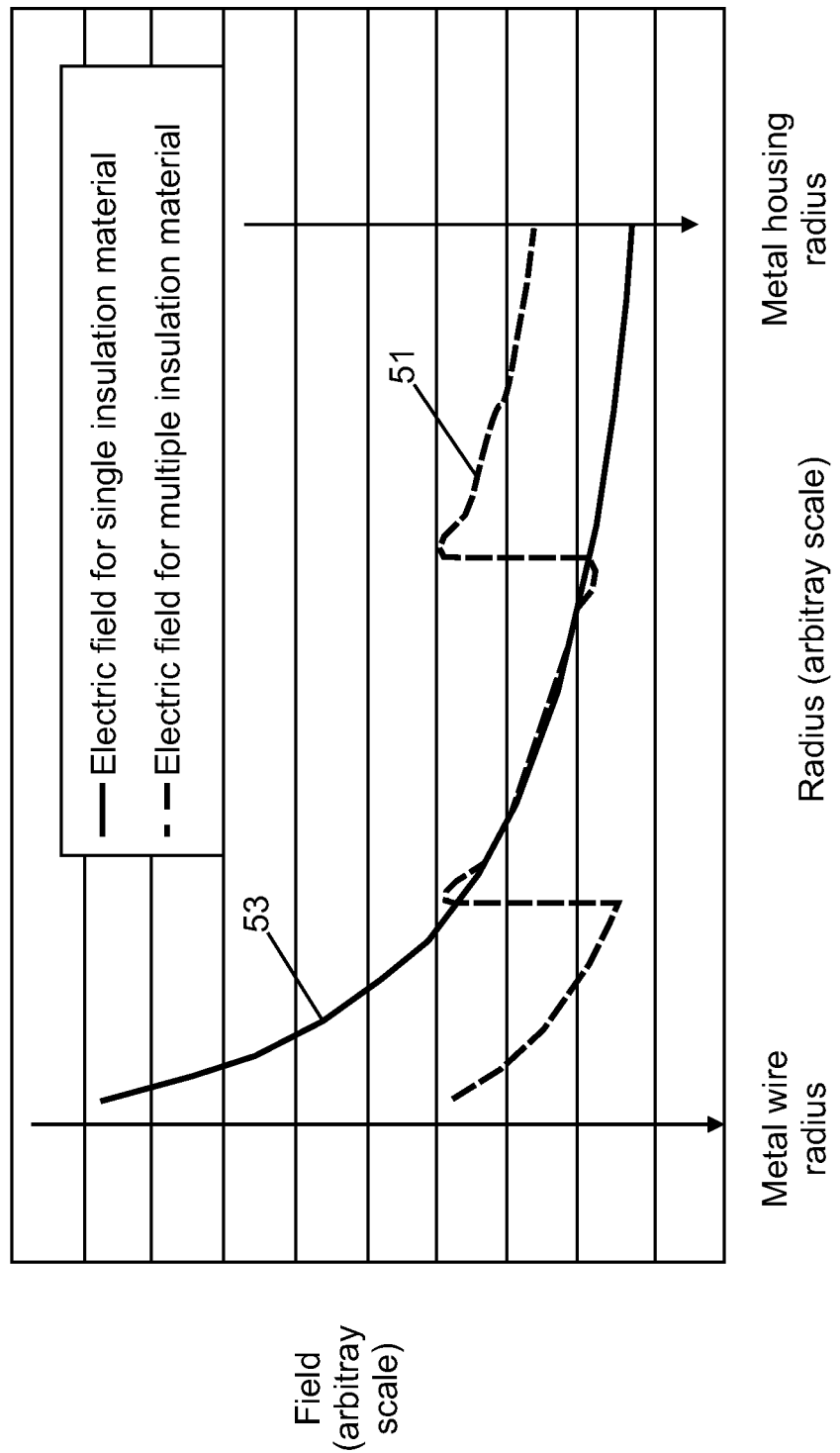
FIG. 4 is a graph showing an electrical field in the offset conduction segment of FIG. 3.

FIG. 4 illustrates an example of the electric field E at various radial distances from the wire 40. The resultant electric field 51 has a maximum in each layer, which is much less than the maximum of an electric field 53 produced in a single layer of insulating or dielectric material. This design thus restricts the maximum field in each insulating material 42 to a level below the material's dielectric strength, and reduces the probability of electric break down in any single insulation layer such as dielectric layer 48, 50 or 52.

Figure 5:
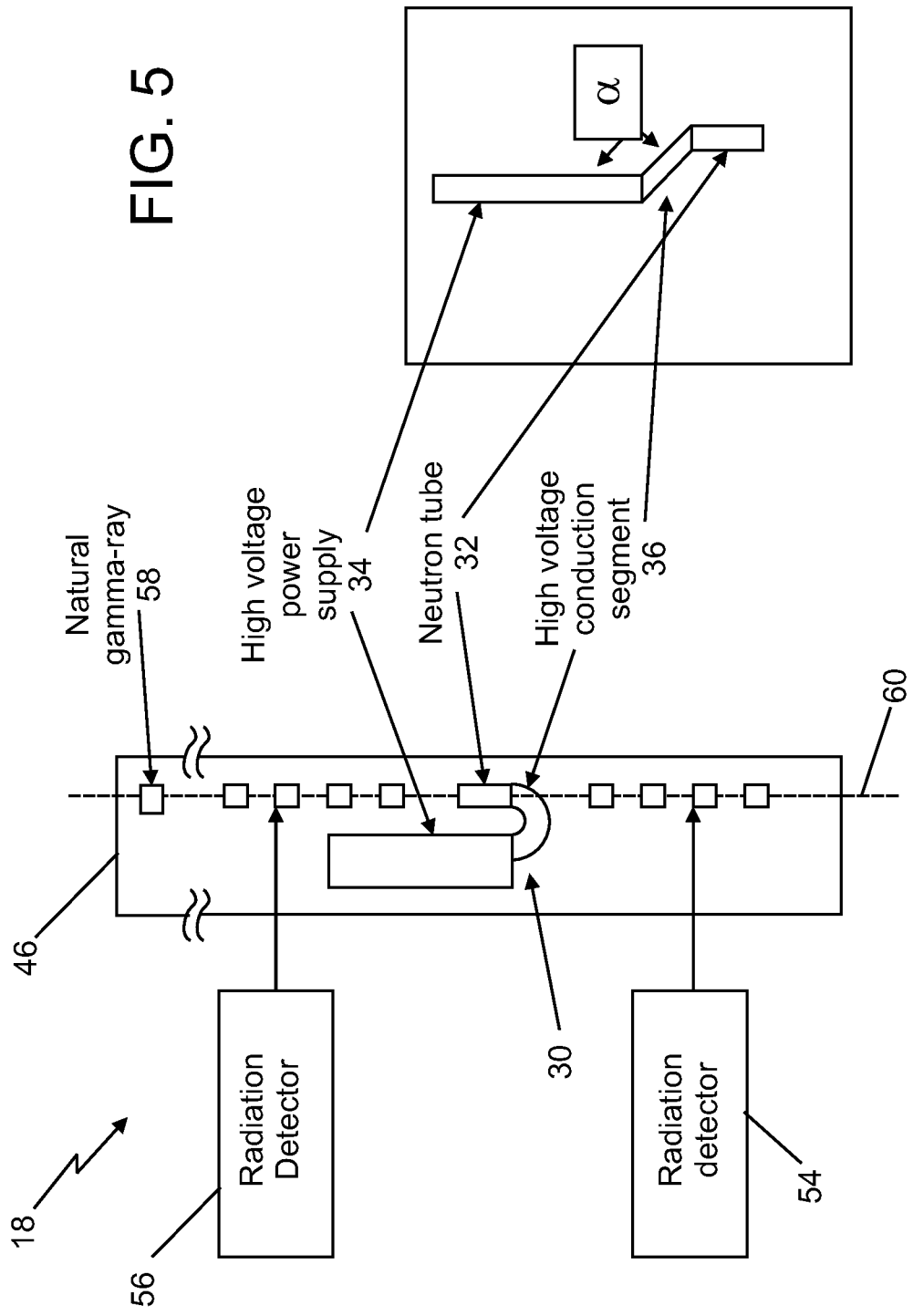
FIG. 5 is a side cross-sectional view of an embodiment of a downhole pulsed neutron measurement tool.

Referring to FIG. 5, an exemplary embodiment of the tool 18 includes a pulsed neutron source or generator 20, 30 and one or more detectors 22. This configuration provides a compact and integrated apparatus for measuring the characteristics of earth formations surrounding a borehole, including thermal or epithermal neutron porosity, sigma, mineralogy, carbon-oxygen ratio, which can be used, for example, as an indication of formation fluid and sourceless density. In one embodiment, the tool 18 is configured as a wireline tool, such as in the system of FIG. 1.

In one embodiment, the detectors 22 are configured as radiation detectors. Such radiation detectors are configured to detect various types of radiation and/or radiation particles such as neutrons, alpha particles, beta particles, x-rays, electrons, protons, gamma rays and others. Examples of radiation detectors include neutron detectors, proton, electron, alpha and beta particle detectors, x-ray and gamma ray detectors, and others. Those skilled in the art will recognize that radiation particles and radiation detectors can take many forms.

The neutron generator 30 includes the neutron tube 32 and the offset HVPS 34 connected to the neutron tube 32 via the offset conduction segment 36. The detectors 22 include various detectors such as radiation detectors 54, 56. For example, radiation detectors 54 may include one or more scintillation gamma ray detectors 54 and radiation detectors 56 may include one or more neutron detectors 56. In one embodiment, one or more additional radiation detectors 58 are included to detect natural background radiation particles emitted from the formation. The additional detectors 58 can be positioned sufficiently far removed and/or shielded from the neutron generator 30. For example, the additional detectors are placed along the leading and/or trailing sides of the tool 18. The additional detectors 58 allow for measuring natural formation radioactive constituents such as K-U-Th along the leading end of the housing 46 and/or activation products along the trailing end. "Leading" and "trailing" ends are defined relative to the location of the neutron tube 32. For example, the leading end is the end of the tool 18 that passes a reference location prior to the neutron tube 32 when the tool 18 is moved during a measurement operation.

The HVPS 34 is located in an offset position relative to the neutron tube 32 so that the detectors 22 can be positioned proximate to the neutron tube 32. This design allows radiation detectors 54, 56 to be placed optimally with respect to the neutron source 32. In one embodiment, a "proximate" location refers to a location that would be unavailable if the HVPS 34 were to be located in line with the neutron tube 32. Examples of such proximate locations include locations adjacent to and/or in the immediate vicinity of the neutron tube 32.

Other proximate locations include locations linearly co-located along an axis with the neutron tube 32. For example, one or more of the radiation detectors 54, 56 are linearly co-located with the neutron tube 32, i.e., placed in line with the neutron tube 32 at the same side in the tool 18. FIG. 5 shows the neutron tube 32 and the radiation detectors 54, 56 located on an axis 60. The axis 60 is, for example, a major axis of the neutron tube 32.

In one embodiment, the radiation detectors 56 are located on the trailing side of the neutron tube 32 since they are insensitive to formation activation gamma rays. If both thermal and epithermal detectors 56 are included, they are small enough that they may be placed side-by-side in the pockets. The positions and sizes of all the radiation detectors 54, 56 can be adjusted for optimized measurement results, and the position of neutron tube 32 can also be adjusted for better measurements.

Figure 6:
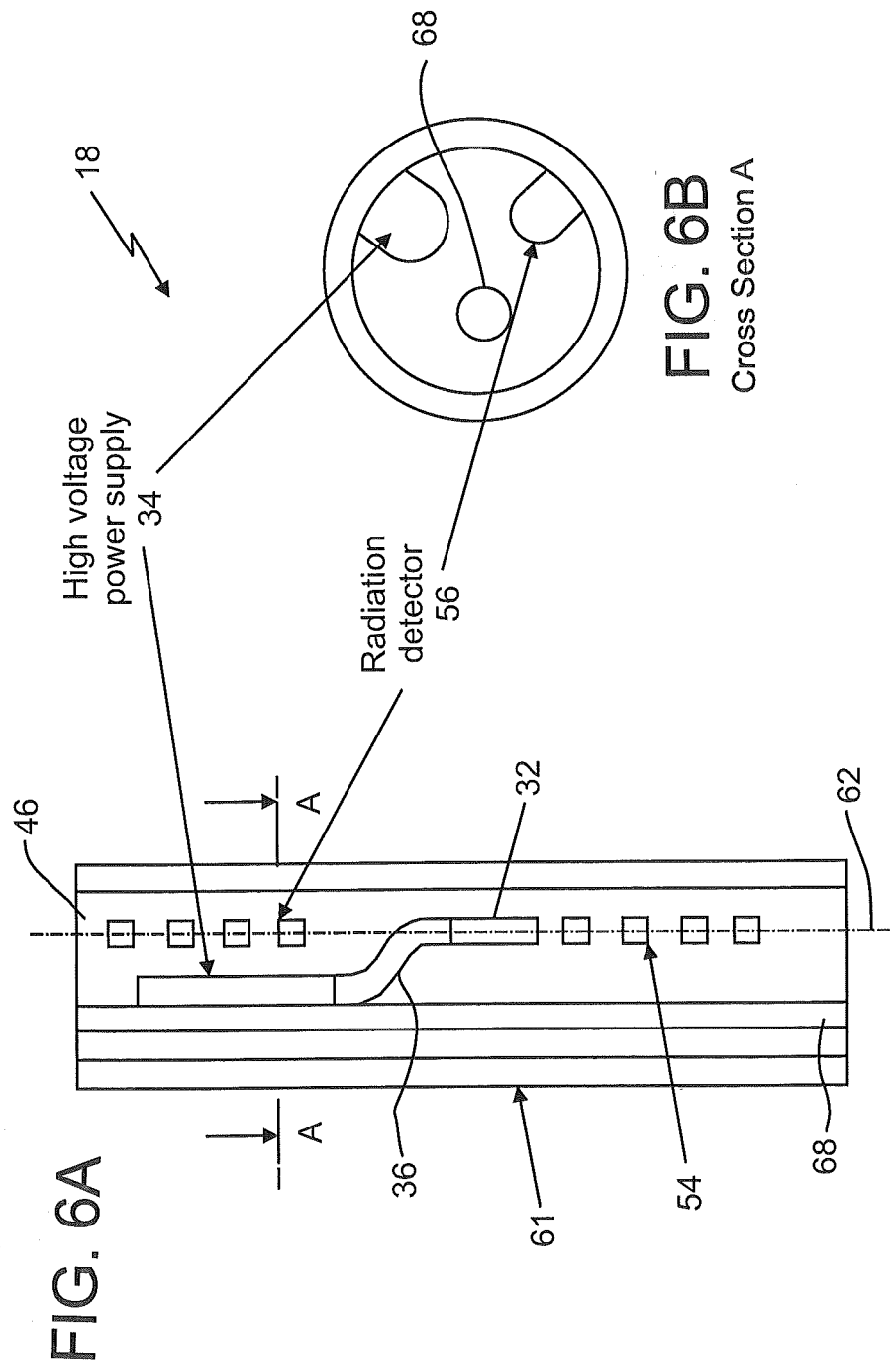
FIGS. 6A and 6B are a side cross-sectional view and an axial cross-sectional view, respectively, of an embodiment of a downhole pulsed neutron measurement tool.
Figure 7:
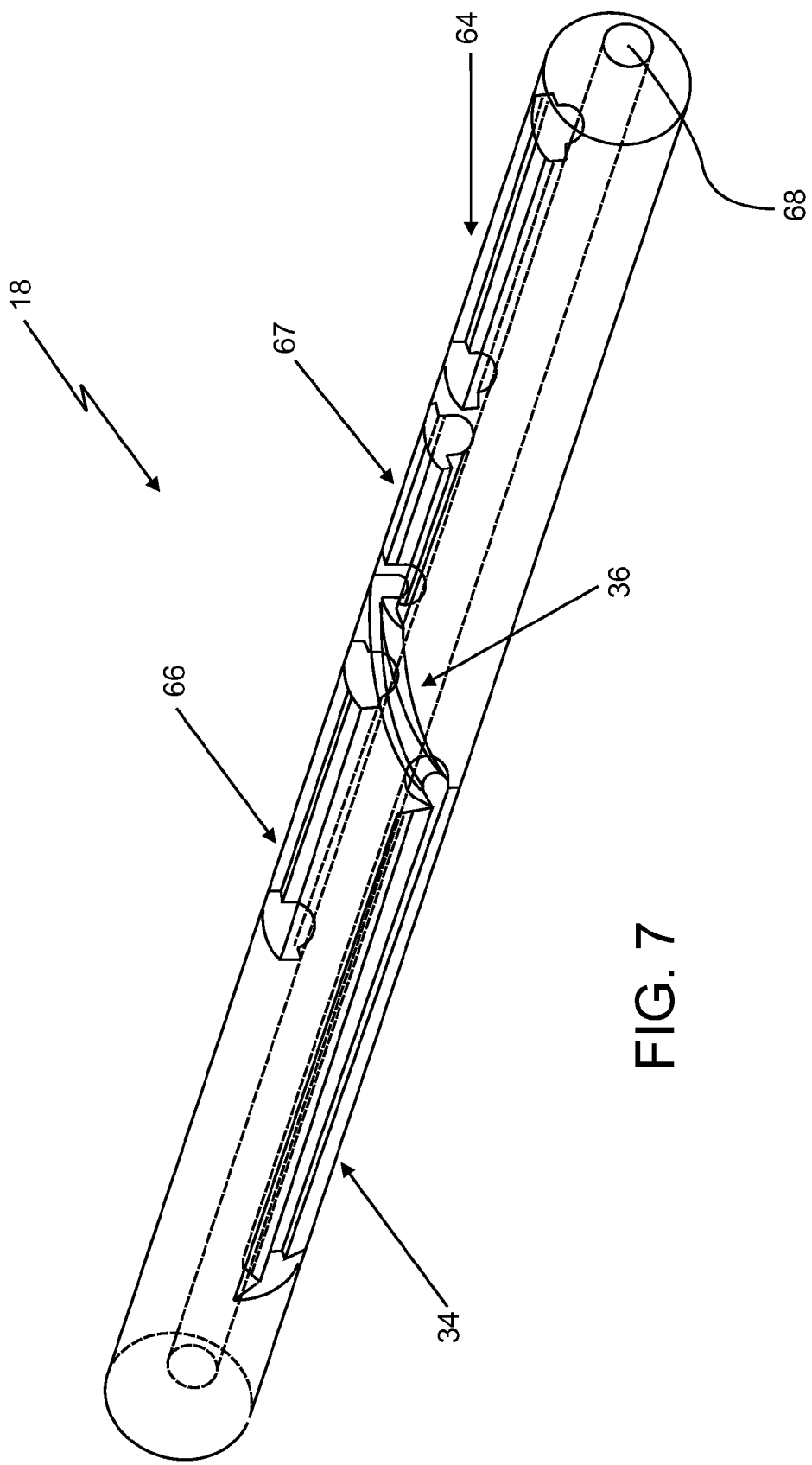
FIG. 7 is a perspective view of the pulsed neutron measurement tool of FIGS. 6A and 6B.

FIGS. 6A, 6B and 7 show an exemplary embodiment of the tool 18. FIGS. 6A and 6B are side and axial cross-sectional views, respectively, of the tool 18, and FIG. 7 is a perspective view of the tool 18. In one embodiment, the tool 18 is configured as a LWD tool, and the housing 46 includes one or more sleeves 61 to protect the neutron generator 30 and the radiation detectors 54, 56. The tool 18, in this embodiment, includes the neutron generator 30 including the neutron tube 32, the offset conductive segment 36 and the HVPS 34. As illustrated, the conduction segment 36 is smoothly curved between the neutron tube 32 and the HVPS 34, although the conduction segment may follow any desired path between the neutron tube 32 and the HVPS 34. One or more radiation detectors 54, 56 are co-located on an axis 62 with the neutron tube 32. For example, radiation detectors 54 may include one or more gamma ray detectors 54 and radiation detectors 56 may include one or more neutron detectors 56.

In one embodiment, the neutron tube 32, the HVPS 34 and/or the radiation detectors 54, 56 are disposed in respective protective housings or chambers. The housings or chambers may be made from materials such as metals sufficient to protect the components from downhole environments or to insulate components. In one example, the radiation detectors 54 are disposed in a corresponding radiation detector chamber 64, the radiation detectors 56 are disposed in a corresponding radiation chamber 66 and the neutron tube 32 is disposed in a neutron tube chamber 67. In FIG. 7, only two chambers for radiation detectors are included, however, there could be any number of chambers for radiation detectors.

In one embodiment, an interior conduit such as a mud channel 68 is disposed in the tool 18, and is configured to connect in fluid communication with the borehole and/or other components of the system 10, such as mud channels in neighboring LWD collars. The mud channel 68 may take any desired path through the tool 18, for example to allow for desired positioning of the radiation detectors 54, 56. For example, a deviated mud channel 68 might be used to allow for other complimentary positioning of detectors to accomplish specific enhancements. In one embodiment, the HVPS 34, the mud channel 68, and the radiation detectors 54, 56 are placed in the same longitudinal region in the housing 46, so that all the components may be distributed uniformly in the housing 46, as shown in FIG. 6B. In one embodiment, the HVPS 34, the neutron tube 32 and/or the detectors 54, 56, 58 are disposed on an interior surface of the housing 46 or an exterior surface of the mud channel 68.

The tool 18 may incorporate a variety of other features and sensors beyond that described in the above embodiments. For example, radiation shielding made from Boron or other suitable materials may be applied inside the housing 46 and/or around selected detectors to eliminate neutron activation of the tool itself. In addition, the tool 18 may include or otherwise be utilized in conjunction with any number of additional measurement tools such as nuclear magnetic resonance (NMR) tools, nuclear quadrapole resonance (NQR) tools, resistivity tools, seismic tools, porosity sensors and others.

The above described systems and/or apparatuses may be employed in a method of estimating at least one property of an earth formation. The method may be performed in conjunction with the system 10 and/or the downhole tool 18, but is not limited thereto.

In a first stage of the method, the pulsed neutron tool 18 is disposed in the borehole 14, and one or more measurements are taken. Measurements are taken by activating the neutron source 20, 30 and detecting resultant gamma ray photons and/or neutrons via the detectors 22, 54, 56 and/or 58. In one embodiment, one or more measurements are taken for each of a plurality of borehole depths. Measurements may include measurements of both capture and inelastic interactions.

Measurements may be taken by supplying power to the pulsed neutron source by activating the HVPS 34 connected to the pulsed neutron tube 32, emitting neutrons from the pulsed neutron tube 32 into the formation, and detecting at least one of neutrons and gamma rays emitted from the formation by the at least one detector.

In one embodiment, the signals generated by the detectors 22, 54, 56 and/or 58 are received and/or processed by the electronics 24 and/or the surface processing unit 28. The signals can be analyzed to determine inelastic and capture measurements, and energy and/or time spectra for the measurements can be calculated.

In one embodiment, the taking of measurements from the tool 18 is recorded in relation to the depth and/or position of the tool 18, which is referred to as "logging", and a record of such measurements is referred to as a "log". Examples of logging processes that can be performed by the system 10 and in conjunction with the methods described herein include measurement-while-drilling (MWD) and logging-while-drilling (LWD) processes. Additional examples of logging processes include logging measurements after drilling, wireline logging, pipe-conveyed logging operations and drop shot logging. The data retrieved during these processes may be transmitted to the surface, and may also be stored with the tool 18 for later retrieval.

In a second stage 42, various properties of the formation are estimated. Examples of such properties include porosity, saturation, sigma values, minerology and a carbon-oxygen ratio.

The apparatuses and methods described herein have various advantages over prior art apparatuses and techniques. The apparatuses and methods allow for placement of detectors in locations proximate to the neutron tube that would otherwise be unavailable in prior art configurations. Prior art configurations generally use a neutron source that includes a HVPS connected adjacent to the neutron tube via a HV coupling unit. A typical prior art source includes a neutron tube and a HVPS packaged together in the same metal cylindrical tube. The apparatuses and methods described herein feature the HVPS connected remotely and/or in an offset position relative to the neutron tube, which allows detectors to be positioned in locations proximate and/or adjacent to the neutron tube that are unavailable in such prior art tools. In addition, the remotely located HVPS may provide more space for scintillation detectors especially in a tool with small radius.

In connection with the teachings herein, various analyses and/or analytical components may be used, including digital and/or analog systems. The system may have components such as a processor, storage media, memory, input, output, communications link (wired, wireless, pulsed mud, optical or other), user interfaces, software programs, signal processors (digital or analog) and other such components (such as resistors, capacitors, inductors and others) to provide for operation and analyses of the apparatus and methods disclosed herein in any of several manners well-appreciated in the art. It is considered that these teachings may be, but need not be, implemented in conjunction with a set of computer executable instructions stored on a computer readable medium, including memory (ROMs, RAMs), optical (CD-ROMs), or magnetic (disks, hard drives), or any other type that when executed causes a computer to implement the method of the present invention. These instructions may provide for equipment operation, control, data collection and analysis and other functions deemed relevant by a system designer, owner, user or other such personnel, in addition to the functions described in this disclosure.

One skilled in the art will recognize that the various components or technologies may provide certain necessary or beneficial functionality or features. Accordingly, these functions and features as may be needed in support of the appended claims and variations thereof, are recognized as being inherently included as a part of the teachings herein and a part of the invention disclosed.

While the invention has been described with reference to exemplary embodiments, it will be understood by those skilled in the art that various changes may be made and equivalents may be substituted for elements thereof without departing from the scope of the invention. In addition, many modifications will be appreciated by those skilled in the art to adapt a particular instrument, situation or material to the teachings of the invention without departing from the essential scope thereof. Therefore, it is intended that the invention not be limited to the particular embodiment disclosed as the best mode contemplated for carrying out this invention.

The invention claimed is:

1. An apparatus for irradiating an earth formation, comprising:
   a carrier configured to be disposed in the formation;
   a neutron tube disposed at the carrier and located on an axis; and
   a high voltage power source disposed at the carrier and electrically connected to the neutron tube, the high voltage power source being offset from the axis; and
   a conduction segment configured to electrically connect the high voltage power supply to the neutron tube, the conduction segment including a high voltage conductor and a plurality of insulating materials surrounding the high voltage conductor, each of the plurality of insulating materials configured to withstand downhole conditions and having a different permittivity, at least one of the plurality of insulating materials being a solid layer of insulating material, the conduction segment including a support structure having the solid layer of insulating material and an outer support tube surrounding the plurality of insulating materials, the support structure configured to maintain the conduction segment along a fixed offset path between the neutron tube and the high voltage power source and maintain each of the plurality of insulating materials at a constant thickness.

2. The apparatus of claim 1, wherein each of the plurality of insulating materials has a thickness that is selected based on the permittivity of the insulating material.

3. The apparatus of claim 2, wherein the thickness of each of the plurality of insulating materials is selected such that the maximum value of an electric field in the insulating material is below a dielectric strength of the material at a downhole temperature.

4. The apparatus of claim 1, wherein the carrier includes a hollow tubular member, and the neutron tube and the high voltage power source are located at an interior of the hollow tubular member.

5. The apparatus of claim 1, wherein at least one of the plurality of insulating materials is a fluid layer, and the support structure is configured to maintain the fluid layer at a constant thickness.

6. The apparatus of claim 5, further comprising an input port configured to introduce insulating fluid into the conduction segment.

7. The apparatus of claim 1, wherein the outer support tube is a conductive tube configured to complete an electrical circuit between the neutron tube and the high voltage power supply.

8. The apparatus of claim 1, wherein the carrier includes an interior conduit.

9. The apparatus of claim 8, wherein the neutron tube and the high voltage power source are disposed on an exterior surface of the conduit.

10. An apparatus for estimating at least one property of an earth formation, comprising:
 a carrier configured to be disposed in the formation;
 at least one detector disposed at the carrier;
 a neutron tube disposed at the carrier and located on an axis;
 a high voltage power source disposed at the carrier and electrically connected to the neutron tube, the high voltage power source being offset from the axis; and
 a conduction segment configured to electrically connect the high voltage power supply to the neutron tube, the conduction segment including a high voltage conductor and a plurality of insulating materials surrounding the high voltage conductor, each of the plurality of insulating materials configured to withstand downhole conditions and having a different permittivity, at least one of the plurality of insulating materials being a solid layer of insulating material, the conduction segment including a support structure having the solid layer of insulating material and an outer support tube surrounding the plurality of insulating materials, the support structure configured to maintain the conduction segment along a fixed offset path between the neutron tube and the high voltage power source and maintain each of the plurality of insulating materials at a constant thickness.

11. The apparatus of claim 10, wherein each of the plurality of insulating materials has a thickness that is selected based on the permittivity of the insulating material.

12. The apparatus of claim 11, wherein the thickness of each of the plurality of insulating materials is selected such that the maximum value of an electric field in the insulating material is below a dielectric strength of the material at a downhole temperature.

13. The apparatus of claim 10, wherein the at least one detector includes at least one radiation detector.

14. The apparatus of claim 10, wherein the carrier includes a hollow tubular member.

15. The apparatus of claim 14, wherein the neutron tube, the at least one detector and the high voltage power source are located at an interior of the hollow tubular member.

16. The apparatus of claim 15, wherein the interior of the hollow tubular member is filled with at least one dielectric material.

17. The apparatus of claim 10, wherein the carrier includes an interior conduit.

18. A method of estimating at least one property of an earth formation, comprising:
 disposing a carrier in a borehole in the earth formation, the carrier including a neutron tube located on an axis and at least one detector;
 supplying power to the neutron tube by activating a high voltage power source electrically connected to the neutron tube via a conduction segment, the high voltage power source being offset from the axis, the conduction segment including a high voltage conductor and a plurality of insulating materials surrounding the high voltage conductor, each of the plurality of insulating materials configured to withstand downhole conditions and having a different permittivity, at least one of the plurality of insulating materials being a solid layer of insulating material, the conduction segment including a support structure having the solid layer of insulating material and an outer support tube surrounding the plurality of insulating materials, the support structure configured to maintain the conduction segment along a fixed offset path between the neutron tube and the high voltage power source and maintain each of the plurality of insulating materials at a constant thickness;
 emitting neutron pulses from the neutron tube into the formation;
 detecting at least one of neutrons and gamma rays emitted from the formation by the at least one detector; and
 estimating the at least one property based on at least one of the detected neutrons and the detected gamma rays.

19. The method of claim 18, wherein each of the plurality of insulating materials has a thickness that is selected such that the maximum value of an electric field in the insulating material is below a dielectric strength of the material at a downhole temperature.

20. The method of claim 18, wherein the at least one property includes at least one of porosity, saturation, sigma, sourceless density, minerology and a carbon-oxygen ratio.

* * * * *